United States Patent [19]

Kobren et al.

[11] Patent Number: 5,611,352

[45] Date of Patent: Mar. 18, 1997

[54] CERVICAL BIOPSY DEVICE

[76] Inventors: Myles S. Kobren; Staci L. Kobren, both of 18 The Grasslands, Woodbury, N.Y. 11797; Joseph C. Segen, 1 Hawthorne La., Manhasset, N.Y. 11030

[21] Appl. No.: 528,249

[22] Filed: Sep. 14, 1995

[51] Int. Cl.⁶ .................................................. A61B 10/00
[52] U.S. Cl. ................................................ 128/751; 128/749
[58] Field of Search ..................................... 128/754, 749, 128/751, 752, 753; 606/174, 170, 162; 16/112

[56] References Cited

U.S. PATENT DOCUMENTS

| | | | |
|---|---|---|---|
| 961,748 | 6/1910 | Allin | 16/112 |
| 4,461,305 | 7/1984 | Cibley . | |
| 4,667,684 | 5/1987 | Leigh . | |
| 4,733,671 | 3/1988 | Mehl . | |
| 4,917,100 | 4/1990 | Nottke . | |
| 4,976,269 | 12/1990 | Menl | 128/754 |
| 5,147,308 | 9/1992 | Singer . | |
| 5,174,300 | 12/1992 | Bales et al. | 128/751 |
| 5,192,294 | 3/1993 | Blake, III . | |
| 5,236,334 | 8/1993 | Bennett . | |
| 5,249,582 | 10/1993 | Taylor | 128/754 |

Primary Examiner—Sam Rimell
Assistant Examiner—Pamela Wingood
Attorney, Agent, or Firm—Larson and Taylor

[57] ABSTRACT

A cervical biopsy device utilizes a biopsy needle having a magnifying lens mounted directly on a cutting sheath. The magnifying lens also acts as a barrier to prevent excessive penetration into the tissue. The components of the biopsy needle, which include a stylet, the cutting sheath and the magnifying lens, may be constructed as a single, disposable unit to eliminate the possibility of blood and/or other fluid contamination when using the biopsy device. In a method of using the biopsy device of the invention, the magnifying lens is used to observe the initial insertion of the stylet and sheath into tissue as well as the cutting and removal of the tissue.

12 Claims, 4 Drawing Sheets

CERVICAL BIOPSY DEVICE

FIELD OF THE INVENTION

The present invention is directed to a biopsy device for obtaining tissue samples and, more particularly, to a disposable, cervical biopsy needle which includes a magnifying lens mounted directly on the cutting sheath.

BACKGROUND OF THE INVENTION

The extraction and analysis of tissue samples has proven a highly effective procedure for identifying cancer, premalignant conditions and other pathology. This procedure has proven particularly effective for identifying pre-invasive cervical lesions, the treatment of which is usually highly successful. Thus, the discussion of the biopsy device of the invention will focus on its use in connection with the analysis of cervical tissue, although it is to be understood that the biopsy device may be used for extraction and analysis of tissue samples in other parts of the body.

Before using a biopsy device to extract and analyze cervical tissue, a doctor will typically conduct an initial screening procedure known as a PAP smear. This screening procedure involves rotating a swab, cytobrush or spatula along the portio cervix or vaginal mucosa to obtain a cell sample which is then spread along a clear slide and analyzed. If the cells appear Atypical with dysplastic features, or reflect low grade or high grade intraepithelium lesions, then a tissue biopsy is usually required.

The most common biopsy device currently used for cervical tissue extraction is a punch biopsy. In order to obtain a tissue sample, a practitioner observes the suspect tissue through a colposcope, which magnifies the tissue, and then uses the punch biopsy to grasp a portion of the tissue and extract it. Major drawbacks of the punch biopsy are that it may cause tissue trauma, disfigurement of the cervix and significant pain. Further, the difficulty in simultaneously using two separate instruments, i.e., viewing the tissue through the colposcope while trying to manipulate the punch biopsy, often results in an inadequate tissue sample. As a result, practitioners often grasp a larger portion of tissue than necessary to ensure that an adequate tissue sample is retrieved. This may result in excessive bleeding requiring cauterization.

One solution to the problem of excessive tissue removal is disclosed by Cibley in U.S. Pat. No. 4,461,305, which is herein incorporated by reference. The Cibley patent discloses a biopsy device comprising a generally cylindrical core-cutter with a rotatably mounted cutting blade. A plunger, slidably mounted within the core-cutter, is used to limit the depth to which the core-cutter advances into the tissue to thereby provide greater control over the sample size. The plunger also provides a means to eject the severed tissue sample. However, it is still possible for the device to penetrate excessively into the tissue. Moreover, like the punch biopsy, this device must be guided using a colposcope.

In addition, both the Cibley device and the punch biopsy are designed for reuse, which is a major drawback in today's infectious-conscious health-care environment where the use of potentially contaminated sharps or other invasive instruments can contribute to the spread of diseases.

Accordingly, the need exists to provide an improved device and method for obtaining tissue samples which reduces the amount of pain and bleeding experienced by a patient.

SUMMARY OF THE INVENTION

Thus, it is a purpose of the present invention to overcome the disadvantages of the prior art and thereby provide a biopsy device and method of use therefor for performing cervical biopsies which eliminates the need to use a colposcope and prevents excessive penetration into tissue.

In accordance with a preferred embodiment, the biopsy device includes a needle attached to a handle. The needle includes a stylet having a sharp tip for insertion into tissue. The stylet has a cradle in an outer surface for collecting a tissue sample. The needle further includes a sheath surrounding a portion of the stylet and movable with respect thereto. The sheath has a cutting edge for cutting tissue and filling the cradle with a tissue sample. A magnifying lens positioned on the sheath allows the tissue to be viewed during the cutting procedure without the need for colposcopic guidance. The magnifying lens also acts as a barrier to prevent excessive penetration into the tissue.

In a preferred embodiment, at least the components of the needle, i.e., the stylet, sheath and magnifying lens, comprise a disposable unit which is attachable to the handle and packaged separately therefrom. The handle preferably has a pistol-type configuration in which a grip portion is pivotally attached to a housing. The needle is attached to the housing and the grip portion may be locked in place at different angles with respect to the needle.

It is, therefore, an object of the present invention to provide a biopsy device which includes a magnifying means which allows tissue to be observed during the cutting procedure and acts as a barrier mechanism to prevent excessive tissue penetration.

It is another object of the invention to provide a relatively inexpensive biopsy device in which the portions having contact with human tissue are disposable.

It is yet another object of the invention to provide a biopsy needle which includes magnifying means mounted directly on the cutting sheath to permit a guided biopsy of the tissue.

It is still another object of the invention to provide a method of performing a cervical biopsy which eliminates the need to perform the biopsy under colposcopic guidance.

These and other objects of the present invention will become apparent from the detailed description to follow.

BRIEF DESCRIPTION OF THE DRAWINGS

There follows a detailed description of the preferred embodiments of the present invention which are to be taken together with the accompanying drawings, wherein.

DESCRIPTION OF THE PREFERRED EMBODIMENTS

Referring now to the figures, like elements are represented by like numerals throughout the several views.

Figure 1:
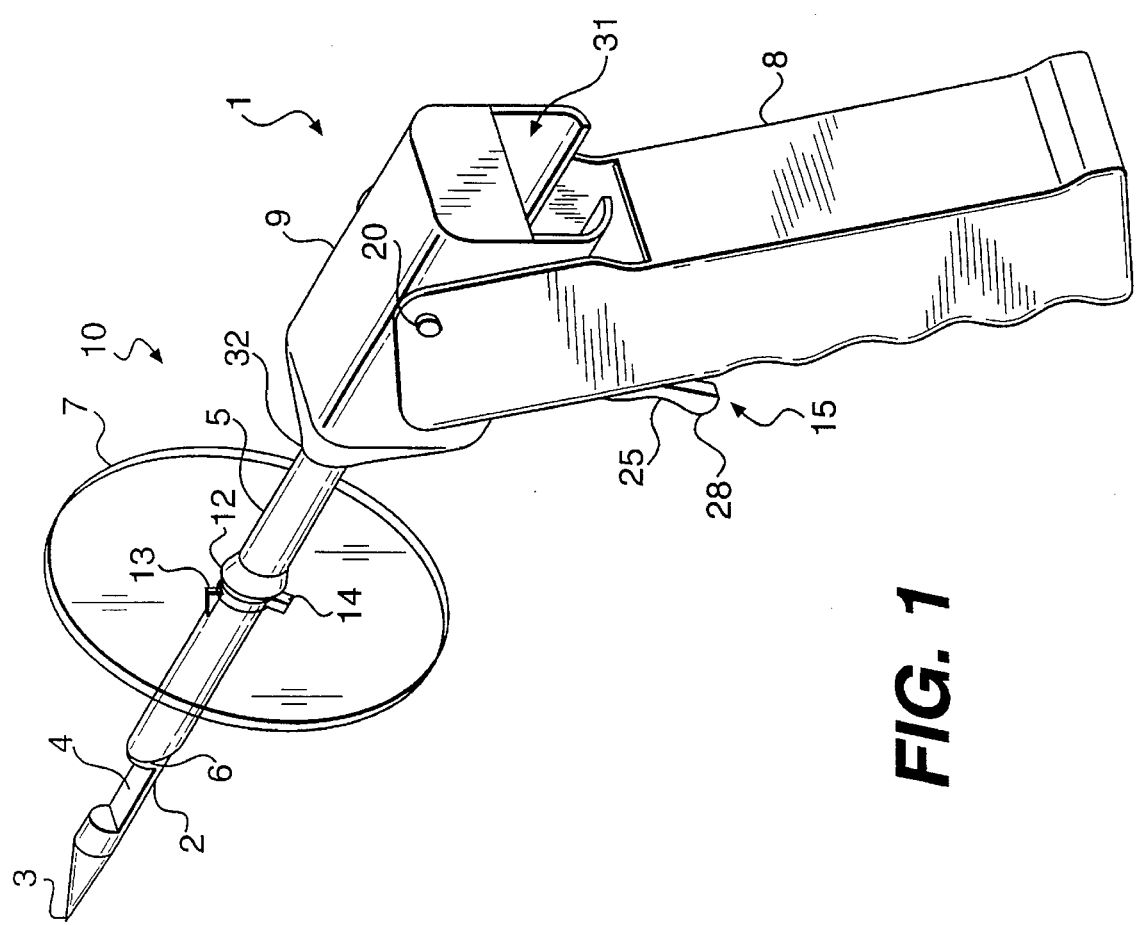
FIG. 1 shows a perspective view of the biopsy device of the invention in a fully assembled form.

FIG. 1 shows the biopsy device of the invention in a fully assembled form and ready for use. The biopsy device includes a handle 1 to which a needle 10 is attached. The needle 10 comprises a stylet 2 having a sharp tip 3 extending outward from the handle 1 for insertion into tissue. The stylet 2 has a cradle 4 in an outer surface between the tip 3 and handle 1 for receiving a tissue sample. The needle 10 further includes a sheath 5 which surrounds a portion of the stylet 2 and is movable thereon. The sheath 5 includes a cutting edge 6 for cutting tissue. The needle 10 also includes a magnifying lens 7 positioned on the sheath 5 to allow the tissue to be observed both during insertion of the stylet 2 into the tissue and during the cutting procedure.

To use the biopsy device of the invention, the practitioner grips the handle 1 and pushes the sheath 5 forward so that the cutting edge 6 moves toward the tip 3 of the stylet 2. The practitioner guides the stylet 2 and sheath 5 into the tissue using the magnifying lens 7 to insure that the stylet 2 is inserted properly. The practitioner then moves the sheath 5 in the reverse direction to expose the cradle 4 whereupon tissue enters the cradle 4. The practitioner pushes the sheath 5 forward again so that the cutting edge 6 moves toward the tip 3 of the stylet 2. As it moves, the cutting edge 6 cuts the tissue and captures a sample within the cradle 4. Because the magnifying lens 7 is located on the sheath 5, the practitioner can observe the entire cutting operation without the need for a colposcope or other separate magnifying means. Once an adequate tissue sample has been collected in the cradle 4, the practitioner then removes the stylet 2 and sheath 5 from the tissue.

Figure 2:
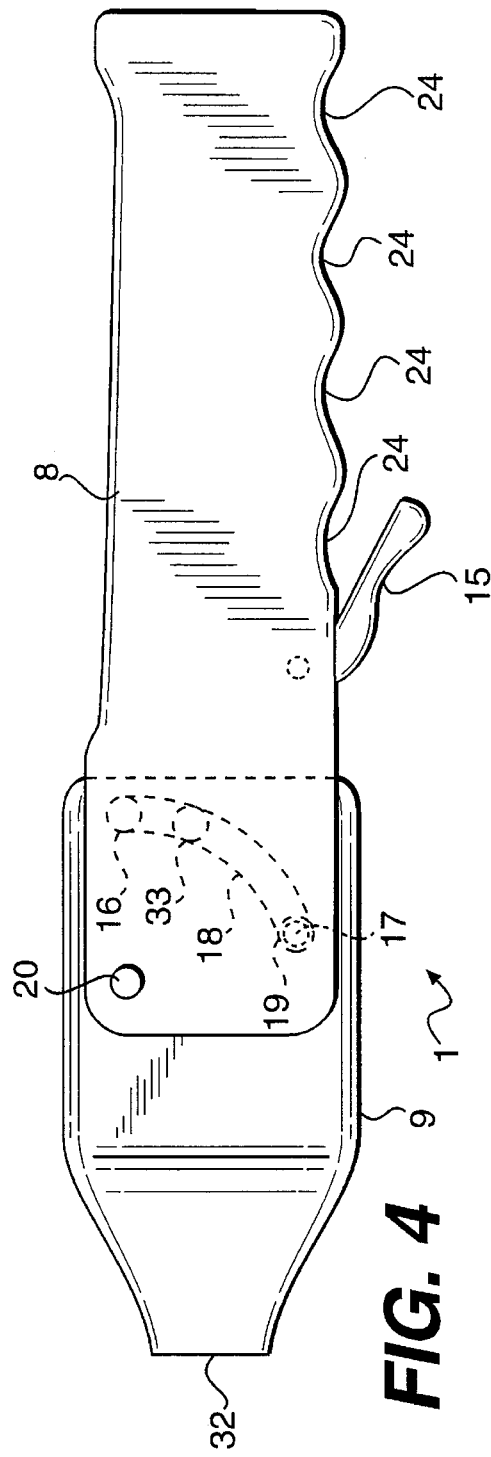
FIG. 2 shows a side view of the biopsy needle of the invention.

Because the various components of the needle 10, i.e., the stylet 2, sheath 5 and magnifying lens 7, contact the tissue during use, it is desirable that these components be separable from the handle 1 for ease in cleaning. Alternatively one or more of these components may be disposable. Most preferably, however, the stylet 2, sheath 5 and magnifying lens 7 are packaged as a single, sterile, disposable unit as shown in FIG. 2, i.e., a unit which is designed for a single use. This ensures complete sterility of the components before each use. In addition, the stylet 2, sheath 5 and magnifying lens 7 can be constructed from relatively low cost materials since they are only intended to last for a single use. The magnifying lens 7, for example, need only be constructed from an inexpensive plastic that provides two to three times magnification.

Even if the stylet 2, sheath 5 and magnifying lens 7 are packaged as a single unit, it is desirable that these individual components be separable to allow greater flexibility when using the biopsy device. For example, when preparing to insert the stylet 2 and sheath 5 into tissue, the practitioner may find that stronger magnification is required. He can then quickly remove the magnifying lens 7 and replace it with a lens having greater magnification.

Figure 3:
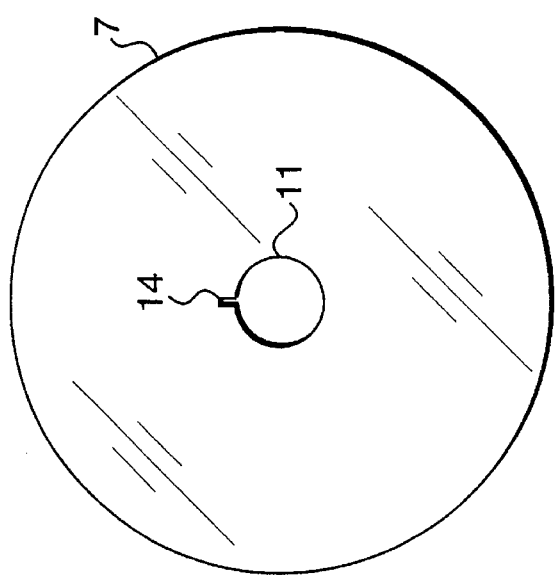
FIG. 3 shows a front view of the magnifying lens.

As shown in FIG. 3, the magnifying lens 7 is in the shape of a circular disk having a central circular opening 11 which is slightly greater in diameter than the sheath 5. The magnifying lens 7 slides over the sheath 5, which has a cylindrical shape, and is held in place between two fixed, raised sections or flanges 12, 13 extending radially outward from the outer wall of the sheath 5, as shown in FIG. 2. In order to position the magnifying lens 7 between the two flanges 12, 13, the central circular opening 11 includes a notch 14 which allows the magnifying lens to slide over flange 13 when notch 14 and flange 13 are aligned. Once in place, the magnifying lens 7 is rotated so that the notch 14 is out of alignment with flange 13 and is thereby held in place between the two flanges 12, 13. Of course, other appropriate configurations for the magnifying glass are considered within the scope of this invention.

Figure 6:
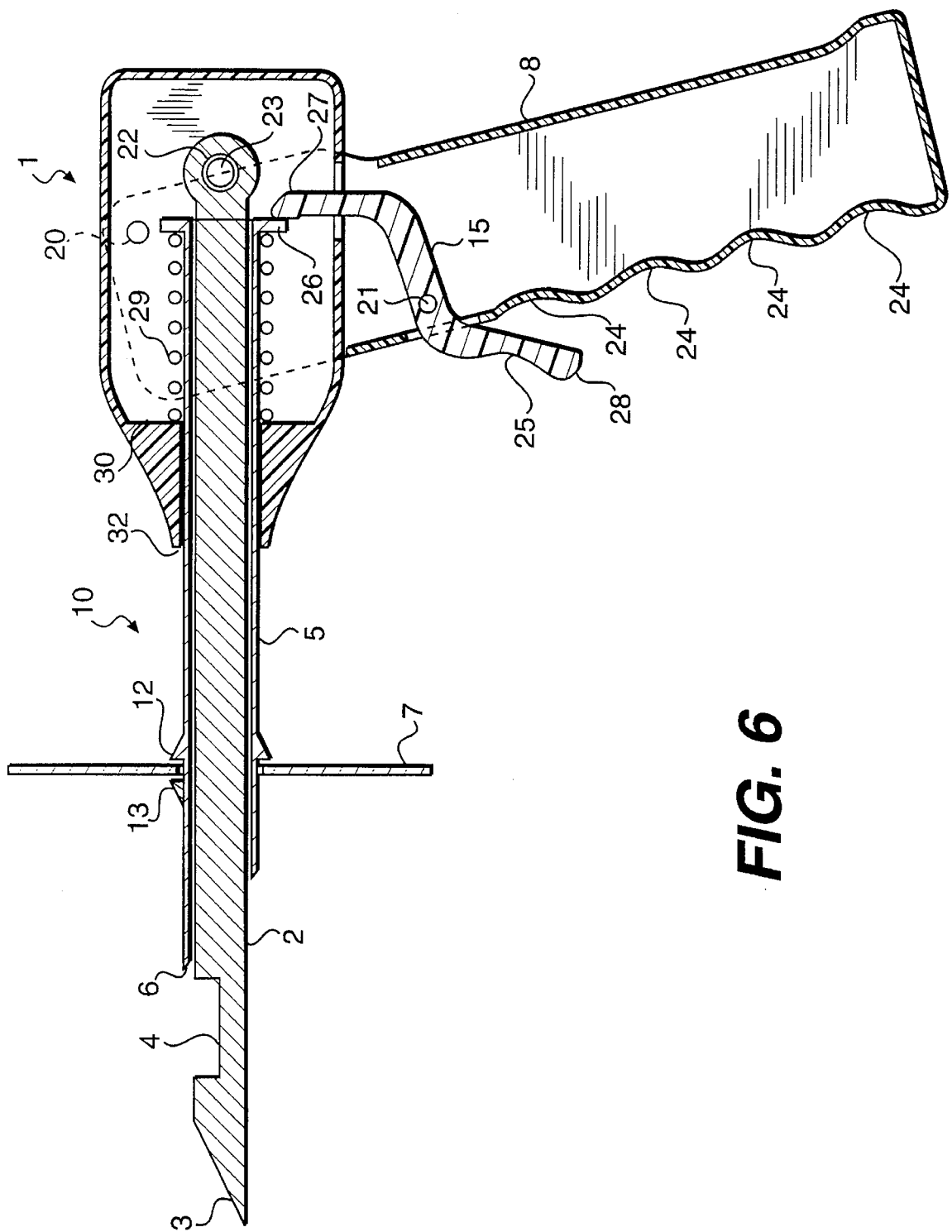
FIG. 6 shows a side cross-sectional view of the biopsy device of the invention taken along a central longitudinal axis of the needle.

Although the size of the components of the biopsy device as well as their positioning with respect to one another may vary considerably, it has been found that an adequate tissue sample may be obtained using a cradle length of about 0.4 to 0.7 centimeters, the thickness of the stylet 2 being approximately 0.25 centimeters, while the outer diameter of the sheath is 0.35 to 0.45 centimeters. The full length of that portion of the stylet 2 which extends outside of the handle 1 is about 5.0 to 8.0 centimeters, with the total combined length of the tip and cradle 4 being less than or equal to about 1.5 centimeters. When the cradle 4 is fully exposed, the magnifying glass 7 should be positioned at a distance of about 1.7 centimeters from the tip 3 of the stylet 2. Thus, the sheath 5 must be positioned on the stylet 2 such that the distance from the far end of the tip 3 to the cutting edge 6 of the sheath is at least 1.5 centimeters, but slightly less than 1.7 centimeters, when the cradle 4 is exposed. The tip 3 and cutting edge 6 should be scalpel sharp. The opposite end of the stylet 2 includes attachment means for attachment to the handle 1. As shown in FIG. 2 and FIG. 6 (discussed in greater detail below), the attachment means may be an eyelet 22 through which a rod 23 in the handle 1 extends. Alternatively, the eyelet 22 may be replaced with a hook (not shown) which hooks onto the rod 23.

The handle 1 may be constructed from a relatively high quality material which is designed to last for multiple uses. The same handle can then be utilized with different stylet sizes or a stronger magnifying lens. Alternatively the handle 1 may be constructed of inexpensive materials and packaged either separately or together with one or more of the stylet 2, sheath 5 and magnifying lens 7, such that the entire biopsy device is disposable.

Although the handle 1 may have any number configurations, a pistol-type configuration, as shown in the figures, has generally proven the most comfortable and easiest to operate with a single hand, leaving the practitioner's other hand free to enable external manipulation or provide other support. The pistol-type configuration includes a grip portion 8 attached to a housing 9 to which the needle 10 is attached. The grip portion 8 may further include grooves 24 where the practitioner's fingers rest. As shown in FIG. 1, the front opening of the housing 32 is typically narrowed to a diameter slightly larger in size than the outer diameter of the sheath 5, but smaller than flange 26 on the sheath (shown more clearly in FIG. 6) to prevent the sheath from sliding out of the housing 9. The rear portion of the housing 9 preferably includes an opening 31 to allow insertion of the needle 10.

Figure 4:
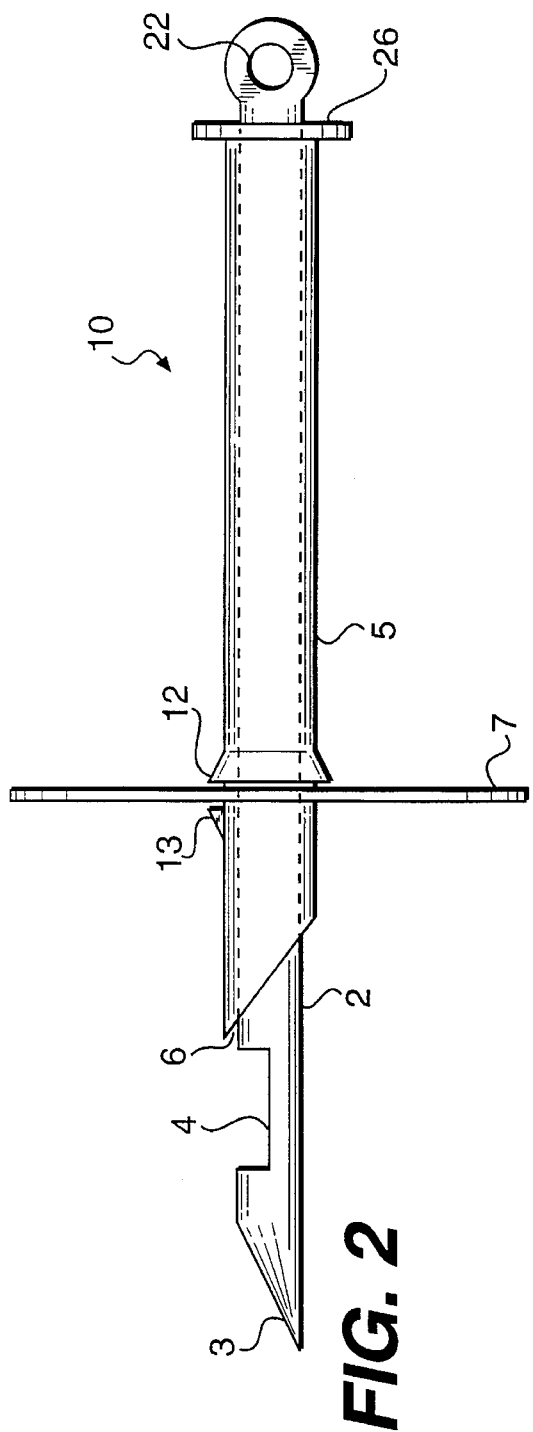
FIG. 4 shows a side view of the handle in which the grip portion is axially aligned with the housing.
Figure 5:
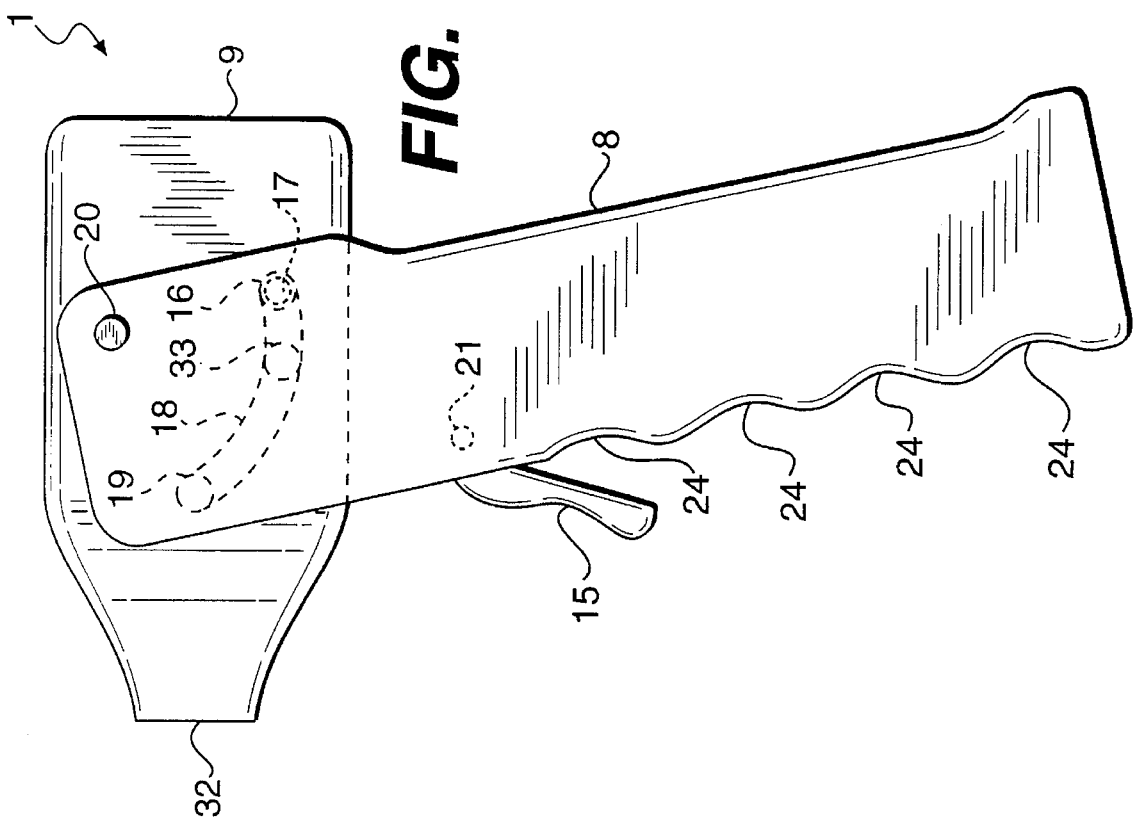
FIG. 5 shows a side view of the handle in which the grip portion is pivoted to a position in which it is almost perpendicular to the housing.

As shown in FIGS. 4 and 5, it is also desirable that the grip portion 8 of the handle 1 be pivotable with respect to the housing 9. This allows the practitioner to rotate the grip portion 8 from a position in which it is virtually perpendicular to the housing 9, shown in FIG. 5 to a position in which the grip portion 8 is linearly aligned with the housing 9, shown in FIG. 4. Although the latter position would generally not be comfortable during use, this position allows greater convenience in packaging the handle since only a narrow rectangular box is required.

The grip portion 8 pivots about a fixed point 20, which may be a rod extending through the housing 9 and grip portion 8. The grip portion 8 is held in place at various angles with respect to the housing 9 using conventional locking means. In the configuration shown, for example, the grip portion 8 includes an arcuate slot 18 in the wall adjacent the housing 9. A spring-actuated protrusion 17, or the like, on the housing 9 extends into the slot 18 to guide the movement of the grip portion 8. The slot 18 includes at least one depression 16 which locks into place with the protrusion 17 on the housing 9 when the grip portion 8 is substantially perpendicular to the biopsy needle 10. Preferably, the slot 18 includes one or more additional depressions 19, 33 which allow the grip portion 8 to be locked into place when it is axially aligned with the biopsy needle 10 or at an angle between the aforementioned positions, respectively.

Although the handle 1 may include various means for moving the sheath 5 forward on the stylet 2, in a preferred embodiment, shown most clearly in FIG. 6, the means for moving the sheath 5 is a trigger 15. A first end 28 of the trigger 15 is exposed and includes a finger engagement portion 25 which is typically engaged by the index finger of the practitioner. A second, opposite end 27 is located inside the housing 9 and rests against the flange 26 or other similar abutment at the end of the sheath 5 opposite the cutting edge 6. The trigger 15 is pivotally attached to the gripping portion 8 at a point 21 between its two ends 27, 28. When the practitioner squeezes the finger engagement portion 25 of trigger 15, the end 27 presses against the flange 26 so that the sheath 5 moves toward the tip 3 of the stylet 2 and covers the cradle portion 4. When the sheath 5 moves forward, a spring 29 positioned between an interior wall 30 in the housing 9 and the flange 26 is compressed. The interior wall 30 also limits the distance that the sheath 5 is movable on the stylet 2. Upon releasing the trigger, the spring 29 returns the sheath 5 to its original position.

Although the invention has been described in considerable detail with respect to preferred embodiments thereof, variations and modifications will be apparent to those skilled in the art without departing from the spirit and scope of the invention as set forth in the claims.

We claim:

1. A biopsy device for extracting tissue, the device comprising:

a handle;

a stylet attached to the handle and having a sharp tip extending outward therefrom for insertion into tissue, the stylet including a cradle in an outer surface between the tip and the handle for receiving tissue;

a sheath surrounding a portion of the stylet and movable with respect thereto, the sheath having a cutting edge for cutting tissue and filling the cradle with a tissue sample;

means for moving the sheath across the cradle; and a transparent barrier means positioned on the sheath and moveable therewith for limiting movement of the stylet and the sheath into tissue.

2. The biopsy device according to claim 1 wherein the handle comprises a housing to which the stylet is attached and a gripping portion pivotally attached to the housing such that the gripping portion is rotatable between a first position in which the gripping portion is axially aligned with the stylet and a second position in which the gripping portion is substantially perpendicular to the stylet.

3. The biopsy device according to claim 2 further comprising locking means for locking the pivotal portion in place in the first position, the second position and at least one position therebetween.

4. The biopsy device according to claim 1 wherein the means for moving comprises a trigger having a first end communicating with an end of the sheath opposite the cutting edge and a second end engagable by a finger of a user.

5. The biopsy device according to claim 4 wherein the end of the sheath opposite the cutting edge is mounted inside the handle and the means for moving further comprises a spring mounted on the sheath between a wall in the housing and a flange extending axially outward from the end of the sheath opposite the cutting edge, the trigger communicating with the flange to compress the spring when a user squeezes the trigger to move the cutting edge of the sheath toward the tip, whereby the sheath is moved away from the tip by a return action of the spring when the trigger is released.

6. The biopsy device according to claim 1 wherein the barrier means comprises a magnifying lens for viewing tissue during use of the biopsy device.

7. A biopsy needle for use in a biopsy device comprising:

a stylet comprising a first end including attachment means for attaching the stylet to a biopsy device, a second end having a sharp tip thereon, and a cradle positioned between the first and second ends for receiving a tissue sample;

a sheath surrounding a portion of the stylet and movable with respect thereto, the sheath having a cutting edge for cutting tissue and filling the cradle with a tissue sample; and a magnifying means positioned on the sheath and moveable therewith for viewing tissue.

8. The biopsy needle according to claim 7 wherein the stylet, the sheath and the magnifying means comprise a disposable unit.

9. The biopsy device according to claim 7 wherein the sheath includes flanges for holding the magnifying means in place.

10. A method of performing a cervical biopsy using a biopsy device comprising a needle attached to a handle, the needle comprising a stylet having a sharp tip thereon and a cradle, a sheath surrounding a portion of the stylet and movable with respect to a longitudinal axis thereof, the sheath having a cutting edge corresponding to the tip of the stylet, and a magnifying means positioned on the sheath and movable therewith, the handle including means for moving the sheath on the stylet, the method comprising the steps of:

moving the cutting edge of the sheath toward the tip of the stylet to cover the cradle;

inserting the stylet and sheath into a wall of a cervix while viewing tissue surrounding the stylet through the magnifying means, said magnifying means limiting a length of the stylet and the sheath which is insertable into the wall;

moving the cutting edge away from the tip to expose the cradle and allow tissue to enter the cradle;

moving the cutting edge in a direction of the tip while viewing the tissue through the magnifying means to cut tissue and collect a tissue sample in the cradle; and removing the needle from the cervix.

11. The biopsy device according to claim 1 wherein the barrier means is positioned on an exterior of the handle.

12. The biopsy device according to claim 7 wherein the magnifying means limits movement of the stylet and sheath into tissue.

* * * * *